(12) United States Patent
Pastore et al.

(10) Patent No.: US 8,886,306 B2
(45) Date of Patent: Nov. 11, 2014

(54) TRIGGERED HIGH-OUTPUT PACING THERAPY

(75) Inventors: Joseph M. Pastore, Concord, OH (US); Shantha Arcot-Krishnamurthy, Vadnais Heights, MN (US); Robert Shipley, Austin, TX (US); Allan C. Shuros, St. Paul, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 930 days.

(21) Appl. No.: 12/535,407

(22) Filed: Aug. 4, 2009

(65) Prior Publication Data

US 2010/0049270 A1    Feb. 25, 2010

Related U.S. Application Data

(60) Provisional application No. 61/090,485, filed on Aug. 20, 2008.

(51) Int. Cl.
*A61N 1/365* (2006.01)
*A61N 1/362* (2006.01)
*A61N 1/368* (2006.01)

(52) U.S. Cl.
CPC ........... *A61N 1/3627* (2013.01); *A61N 1/36521* (2013.01); *A61N 1/36564* (2013.01); *A61N 1/36592* (2013.01); *A61N 1/3688* (2013.01); *A61N 1/36578* (2013.01)
USPC .................................. 607/9; 607/17; 607/23

(58) Field of Classification Search
USPC ................................ 607/9, 18–20, 22–23, 17
See application file for complete search history.

(56) References Cited

U.S. PATENT DOCUMENTS

| | | | |
|---|---|---|---|
| 5,184,615 A | 2/1993 | Nappholz et al. | |
| 5,213,098 A | 5/1993 | Bennett et al. | |
| 7,356,366 B2 | 4/2008 | Sweeney et al. | |
| 8,131,363 B2 * | 3/2012 | Arcot-Krishnamurthy et al. | 607/22 |
| 2003/0199933 A1 * | 10/2003 | Struble | 607/17 |
| 2004/0049235 A1 * | 3/2004 | Deno et al. | 607/9 |
| 2004/0106953 A1 * | 6/2004 | Yomtov et al. | 607/3 |
| 2004/0220637 A1 * | 11/2004 | Zdeblick et al. | 607/17 |
| 2005/0075675 A1 * | 4/2005 | Mulligan et al. | 607/9 |
| 2006/0247699 A1 | 11/2006 | Burnes et al. | |
| 2007/0191921 A1 * | 8/2007 | Zhu et al. | 607/120 |
| 2007/0299477 A1 * | 12/2007 | Kleckner et al. | 607/9 |
| 2008/0086185 A1 | 4/2008 | Amurthur et al. | |
| 2008/0177344 A1 * | 7/2008 | Maskara et al. | 607/25 |
| 2009/0082825 A1 | 3/2009 | Arcot-Krishnamurthy et al. | |

FOREIGN PATENT DOCUMENTS

WO    WO-01/58518 A2    8/2001

OTHER PUBLICATIONS

"International Application Serial No. PCT/US2008/011057, International Search Report mailed Jan. 8, 2009", 3 pgs.
"International Application Serial No. PCT/US2008/011057, Written Opinion mailed Jan. 8, 2009", 7 pgs.

(Continued)

*Primary Examiner* — Niketa Patel
*Assistant Examiner* — Christopher A Flory
(74) *Attorney, Agent, or Firm* — Schwegman Lundberg & Woessner, P.A.

(57) ABSTRACT

A device and method for delivering electrical stimulation to the heart in order to improve cardiac function in heart failure patients. The stimulation is delivered as high-output pacing in which the stimulation is excitatory and also of sufficient energy to augment myocardial contractility. The device may be configured to deliver high-output pacing upon detection of cardiac decompensation.

18 Claims, 6 Drawing Sheets

(56) References Cited

OTHER PUBLICATIONS

Burkhoff, D., et al., "Nonexcitatory electrical signals for enhancing ventricular contractility: rationale and initial investigations of an experimental treatment for heart failure.", *Am J Physiol Heart Circ Physiol.*, 288(6), (Jun. 2005), H2550-H2556.

Marrouche, N. F., et al., "Nonexcitatory stimulus delivery improves left ventricular function in hearts with left bundle branch block.", *J Cardiovasc Electrophysiol.*, 13(7), (Jul. 2002), 691-695.

Mohri, S., et al., "Cardiac contractility modulation by electric currents applied during the refractory period.", *Am J Physiol Heart Circ Physiol.* May 2002;282(5):, (May 2002), H1642-H1647.

Morita, H., et al., "Long-term effects of non-excitatory cardiac contractility modulation electric signals on the progression of heart failure in dogs.", *Eur J Heart Fail.*, 6(2), (Mar. 1, 2004), 145-150.

O'Connell, J. B., "The Economic Burden of Heart Failure", *Clinical Cardiology*, 23(Suppl. 3), (2000), III6-III10.

Olson, R. D., et al., "Quantification of the Voltage-Response Relationship Between Punctate and Field Electrical Stimulation and the Function of Isolated Rat Left Atria and Papillary Muscles", *Journal of Pharmacological and Toxicological Methods*, 34(4), (Dec. 1995), 225-230.

Pappone, C., et al., "Cardiac contractility modulation by electric currents applied during the refractory period in patients with heart failure secondary to ischemic or idiopathic dilated cardiomyopathy.", *Am J Cardiol.*, 90(12), (Dec. 15, 2002), 1307-13.

Pappone, C., et al., "First human chronic experience with cardiac contractility modulation by nonexcitatory electrical currents for treating systolic heart failure: mid-term safety and efficacy results from a multicenter study.", *J Cardiovasc Electrophysiol.*, 15(4), (Apr. 2004), 418-27.

Thom, T., et al., "Heart Disease and Stroke Statistics—2005 Update / A Report From the American Heart Association Statistics Committee and Stroke Statistics Subcommittee", *Circulation*, 113, (Correction, Circulation, 114, (2006), p. e630), (2006), e85-e151.

\* cited by examiner

TRIGGERED HIGH-OUTPUT PACING THERAPY

CROSS REFERENCE TO RELATED APPLICATIONS

This application claims the benefit of U.S. Provisional Application No. 61/090,485, filed on Aug. 20, 2008, under 35 U.S.C. §119(e), which is hereby incorporated by reference in its entirety.

This application is related to U.S. patent application Ser. No. 11/860,957 filed on Sep. 25, 2007, now U.S. Pat. No. 8,131,363, and assigned to Cardiac Pacemakers, Inc., the disclosure of which is incorporated by reference in its entirety.

FIELD OF THE INVENTION

This invention pertains to apparatus and methods for the treatment of heart disease and to devices providing electrostimulation to the heart such as cardiac pacemakers.

BACKGROUND

Heart failure (HF) is a debilitating disease that refers to a clinical syndrome in which an abnormality of cardiac function causes a below normal cardiac output that can fall below a level adequate to meet the metabolic demand of peripheral tissues. Heart failure can be due to a variety of etiologies with ischemic heart disease being the most common. Heart failure is usually treated with a drug regimen designed to augment cardiac function and/or relieve congestive symptoms.

Electrostimulation of the ventricles can also be useful in treating heart failure. It has been shown that some heart failure patients suffer from intraventricular and/or interventricular conduction defects (e.g., bundle branch blocks) such that their cardiac outputs can be increased by improving the synchronization of ventricular contractions with electrical stimulation. In order to treat these problems, implantable cardiac devices have been developed that provide appropriately timed electrical stimulation to one or more heart chambers in an attempt to improve the coordination of atrial and/or ventricular contractions, termed cardiac resynchronization therapy (CRT). Ventricular resynchronization is useful in treating heart failure because, although not directly inotropic, resynchronization can result in a more coordinated contraction of the ventricles with improved pumping efficiency and increased cardiac output. Currently, a most common form of CRT applies stimulation pulses to both ventricles, either simultaneously or separated by a specified biventricular offset interval, and after a specified atrio-ventricular delay interval with respect to the detection of an intrinsic atrial contraction or delivery of an atrial pace.

It has also been demonstrated that electrostimulatory pulses delivered to the heart during its refractory period can augment myocardial contractility. Applying contractility augmenting stimulation to the ventricles can thus aid in the treatment of heart failure. Such stimulation, sometimes referred to as cardiac contractility modulation (CCM), can be delivered during the refractory period after an intrinsic contraction and hence is non-excitatory. Presumably, such stimulation increases myocardial contractility by increasing intracellular calcium concentration and/or eliciting release of neurotransmitters.

DETAILED DESCRIPTION

Figure 1:
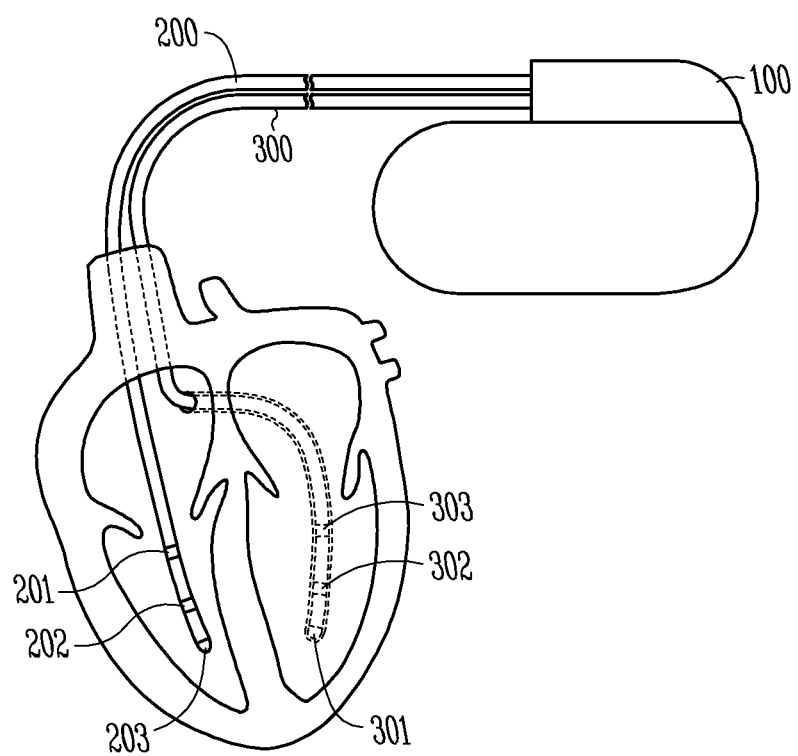
FIG. 1 illustrates the physical configuration of an exemplary pacing device.

As noted above, CCM stimulation can be delivered in a non-excitatory manner during the refractory period after an intrinsic contraction. It has been found that such non-excitatory CCM stimulation enhances contractility in a generally consistent manner such that contractility is enhanced for every beat and is relatively insensitive to variations in stimulation parameters such as stimulation pulse duration, and stimulation timing. Contractility augmenting stimulation can also be applied in an excitatory manner, however, referred to herein as high-output pacing (HOP). In one form of HOP, the stimulation is delivered in the same manner as conventional pacing using a bradycardia pacing mode using stimulation pulses with a higher stimulation energy. For example, a stimulation pulse for high-output pacing may be a biphasic (or multiphasic) waveform having a peak-to-peak voltage amplitude of + or −5-8 volts and a pulse duration of 50-70 milliseconds. In another form of HOP, similar stimulation pulses are delivered in the refractory period following a conventional ventricular pacing pulse. Unlike as is the case for non-excitatory CCM, it has been found that HOP is sensitive to stimulation parameters such as the stimulation site, stimulation pulse duration, and stimulation timing. Unless those parameters are optimized, contractility enhancement by HOP is inconsistent from beat to beat. This disclosure describes methods and devices for delivering HOP in which stimulation parameters are optimized in accordance with a measured hemodynamic response.

An exemplary device for delivering HOP stimulation may be a device with the capability for also delivering bradycardia pacing, CRT, cardioversion/defibrillation shocks, and/or neural stimulation. The device is equipped with multiple stimulation electrodes that can be placed at different sites in the ventricle and/or atrium by means of unipolar or multipolar leads. The stimulation electrodes are switchably connected to pulse generation circuitry for delivering stimulation pulses to selected stimulation sites. The HOP stimulation pulses can be delivered from one or multiple stimulation electrodes, either simultaneously or with timing offsets between them. In order to optimize the stimulation parameters, the device is configured to measure the hemodynamic response while the HOP is delivered from single or multiple sites and to adjust the stimulation parameters in a manner that results in the most improvement. In order to measure hemodynamic response, the device is equipped with the capability of measuring one or more physiological variables that are reflective of myocardial contractility. Examples of such variables include heart sound amplitudes (e.g., the amplitude of the sound mitral valve closure during systole), systolic blood pressure, or cardiac stroke volume (e.g., as measured by a transthoracic impedance sensor). The stimulation site or sites, the amplitude of stimulation, the polarity (only positive, only negative, biphasic, unbalanced waveforms), the stimulation pulse duration, the number of pulses and the timing of the stimulation pulses may then be adjusted in order to maximally augment contractility. The stimulation parameter optimization procedure involves delivering HOP with particular stimulation parameters and measuring the hemodynamic response as the stimulation parameters are changed in some prescribed manner. The stimulation parameter optimization procedure may be performed at periodic intervals, upon command received via telemetry, or in response to one or more measured parameters that indicate the patient's clinical status may have changed. Examples of the latter could include the hemodynamic response parameters used in the stimulation parameter optimization procedure or other parameters such as heart rate, heart rate variability, or other measures of autonomic tone. The device may be configured to deliver HOP either continuously or intermittently. In the latter case, the device enters an HOP mode according to specified entry and exit conditions where the specified entry and exit conditions may be lapsed time intervals, sensed parameter values, or combinations thereof.

1. Exemplary Cardiac Device

FIG. 1 shows an implantable cardiac pacing device 100 for delivering pacing therapy including HOP. Implantable pacing devices are typically placed subcutaneously or submuscularly in a patient's chest with leads threaded intravenously into the heart to connect the device to electrodes disposed within a heart chamber that are used for sensing and/or pacing of the chamber. Electrodes may also be positioned on the epicardium by various means. A programmable electronic controller causes the pacing pulses to be output in response to lapsed time intervals and/or sensed electrical activity (i.e., intrinsic heart beats not as a result of a pacing pulse). The device senses intrinsic cardiac electrical activity through one or more sensing channels, each of which incorporates one or more of the electrodes. In order to excite myocardial tissue in the absence of an intrinsic beat, pacing pulses with energy above a certain threshold are delivered to one or more pacing sites through one or more pacing channels, each of which incorporates one or more of the electrodes. FIG. 1 shows the exemplary device having two leads 200 and 300, each of which is a multi-polar (i.e., multi-electrode) lead having electrodes 201-203 and 301-303, respectively. The electrodes 201-203 are disposed in the right ventricle in order to stimulate or sense right ventricular or septal regions, while the electrodes 301-303 are disposed in the coronary sinus in order to stimulate or sense regions of the left ventricle. Other embodiments may use any number of electrodes in the form of unipolar and/or multi-polar leads in order to sense or stimulate different myocardial sites. Once the device and leads are implanted, the pacing and/or sensing channels of the device may be configured with selected ones of the multiple electrodes in order to selectively stimulate or sense a particular myocardial site(s). As described below, the pacing channels may be used to deliver conventional bradycardia pacing, CRT, or HOP therapy.

Figure 2:
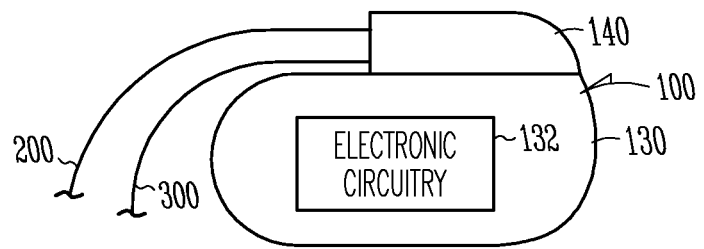
FIG. 2 shows the components of an exemplary device.

FIG. 2 shows the components of the implantable device 100 in more detail. The implantable device 100 includes a hermetically sealed housing 130 that is placed subcutaneously or submuscularly in a patient's chest. The housing 130 may be formed from a conductive metal, such as titanium, and may serve as an electrode for delivering electrical stimulation or sensing in a unipolar configuration. A header 140, which may be formed of an insulating material, is mounted on the housing 130 for receiving leads 200 and 300 which may be then electrically connected to pulse generation circuitry and/or sensing circuitry. Contained within the housing 130 is the electronic circuitry 132 for providing the functionality to the device as described herein which may include a power supply, sensing circuitry, pulse generation circuitry, a programmable electronic controller for controlling the operation of the device, and a telemetry transceiver capable of communicating with an external programmer or a remote monitoring device.

Figure 3:
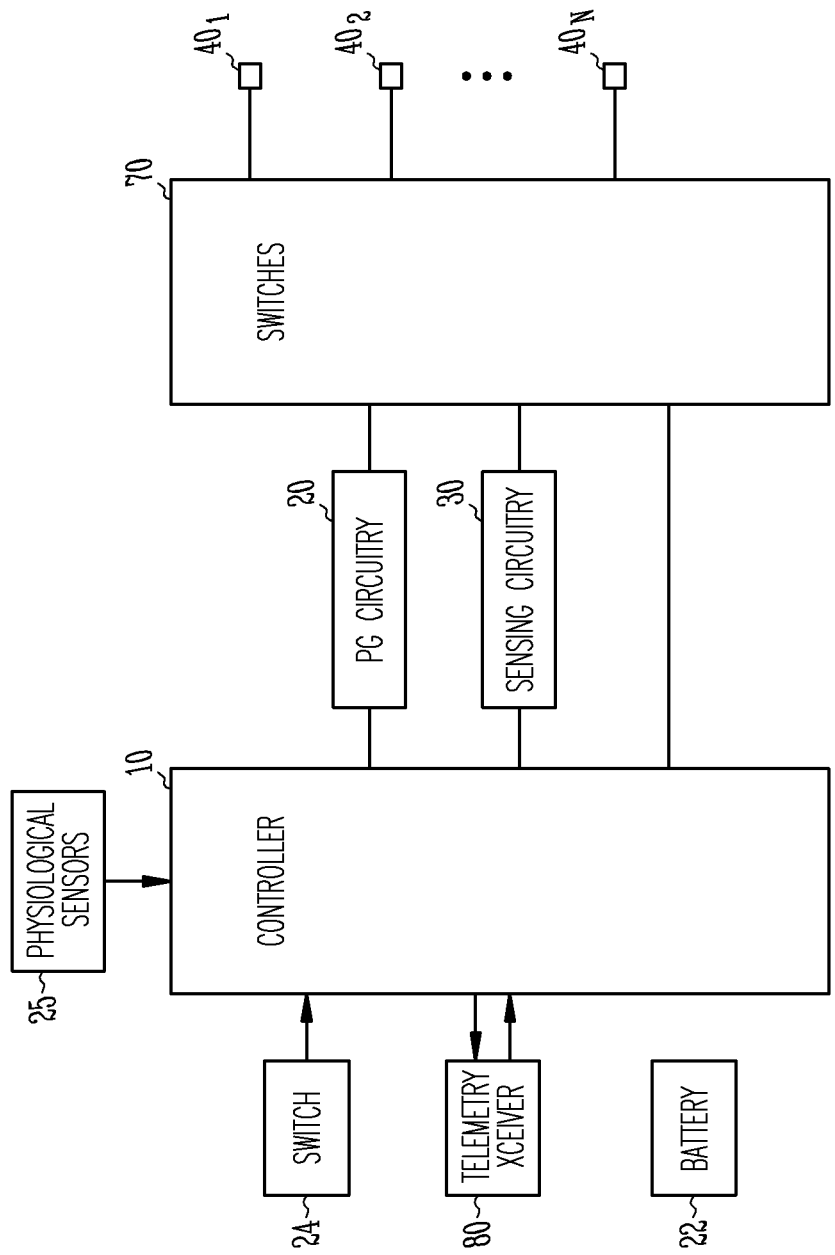
FIG. 3 is a block diagram of the electronic circuitry of an exemplary device.

FIG. 3 shows a system diagram of the electronic circuitry 132. A battery 22 supplies power to the circuitry. The controller 10 controls the overall operation of the device in accordance with programmed instructions and/or circuit configurations. The controller may be implemented as a microprocessor-based controller and include a microprocessor and memory for data and program storage, implemented with dedicated hardware components such as ASICs (e.g., finite state machines), or implemented as a combination thereof. The controller also includes timing circuitry such as external clocks for implementing timers used to measure lapsed intervals and schedule events. As the term is used herein, the programming of the controller refers to either code executed by a microprocessor or to specific configurations of hardware components for performing particular functions. Interfaced to the controller are sensing circuitry 30 and pulse generation circuitry 20 by which the controller interprets sensing signals and controls the delivery of paces and/or HOP stimulation pulses in accordance with a pacing mode. The controller is capable of operating the device in a number of programmed pacing modes which define how pulses are output in response to sensed events and expiration of time intervals. The controller also implements timers derived from external clock signals in order to keep track of time and implement real-time operations such as scheduled entry into a HOP mode.

The sensing circuitry 30 receives atrial and/or ventricular electrogram signals from sensing electrodes and includes sensing amplifiers, analog-to-digital converters for digitizing sensing signal inputs from the sensing amplifiers, and registers that can be written to for adjusting the gain and threshold values of the sensing amplifiers. The sensing circuitry of the pacemaker detects a chamber sense, either an atrial sense or ventricular sense, when an electrogram signal (i.e., a voltage sensed by an electrode representing cardiac electrical activity) generated by a particular channel exceeds a specified detection threshold. Pacing algorithms used in particular pacing modes employ such senses to trigger or inhibit pacing, and the intrinsic atrial and/or ventricular rates can be detected by measuring the time intervals between atrial and ventricular senses, respectively. The pulse generation circuitry 20 delivers conventional pacing and/or HOP pulses to pacing electrodes disposed in the heart and includes capacitive discharge or current source pulse generators, registers for controlling the pulse generators, and registers for adjusting parameters such as pulse energy (e.g., pulse amplitude and width). The pulse generation circuitry may also include a shocking pulse generator for delivering a defibrillation/cardioversion shock via a shock electrode upon detection of a tachyarrhythmia.

A telemetry transceiver 80 is interfaced to the controller which enables the controller to communicate with an external device such as an external programmer and/or a remote monitoring unit. An external programmer is a computerized device with an associated display and input means that can interrogate the pacemaker and receive stored data as well as directly adjust the operating parameters of the pacemaker. The external device may also be a remote monitoring unit that may be interfaced to a patient management network enabling the implantable device to transmit data and alarm messages to clinical personnel over the network as well as be programmed remotely. The network connection between the external device and the patient management network may be implemented by, for example, an internet connection, over a phone line, or via a cellular wireless link. A switch 24 is also shown as interfaced to the controller in this embodiment to allow the patient to signal certain conditions or events to the implantable device. In different embodiments, the switch 24 may be actuated magnetically, tactilely, or via telemetry such as by a hand-held communicator. The controller may be programmed to use actuation of the switch 24 to as an entry and/or exit condition for entering a HOP mode.

A pacing channel is made up of a pulse generator connected to an electrode, while a sensing channel is made up of a sense amplifier connected to an electrode. Shown in the figure are electrodes $40_1$ through $40_N$ where N is some integer. The electrodes may be on the same or different leads and are electrically connected to a MOS switch matrix 70. The switch matrix 70 is controlled by the controller and is used to switch selected electrodes to the input of a sense amplifier or to the output of a pulse generator in order to configure a sensing or pacing channel, respectively. The device may be equipped with any number of pulse generators, amplifiers, and electrodes that may be combined arbitrarily to form sensing or pacing channels. The device is therefore capable of delivering single-site or multiple site ventricular pacing and/or HOP stimulation. The switch matrix 70 also allows selected ones of the available implanted electrodes to be incorporated into sensing and/or pacing channels in either unipolar or bipolar configurations. A bipolar sensing or pacing configuration refers to the sensing of a potential or output of a pacing pulse between two closely spaced electrodes, where the two electrodes are usually on the same lead (e.g., a ring and tip electrode of a bipolar lead or two selected electrodes of a multi-polar lead). A unipolar sensing or pacing configuration is where the potential sensed or the pacing pulse output by an electrode is referenced to the conductive device housing or another distant electrode.

The device may also include one or more physiological sensing modalities 25 for use in controlling the pacing rate, optimization of HOP stimulation parameters, and/or the initiation/cessation of the HOP mode. One such sensing modality is an accelerometer that enables the controller to detect changes in the patient's physical activity, detect patient posture (i.e., using a multi-axis accelerometer), and/or detect heart sounds. A dedicated acoustic sensor that may be of various types may also be used to detect heart sounds. An impedance sensor may be configured with electrodes for measuring minute ventilation for use in rate adaptive pacing and/or for measuring cardiac stroke volume or cardiac output. The device may also include a pressure sensor that may be used, for example, to measure pressure in the pulmonary artery or elsewhere.

2. Optimization of HOP Stimulation Parameters

Figure 4:
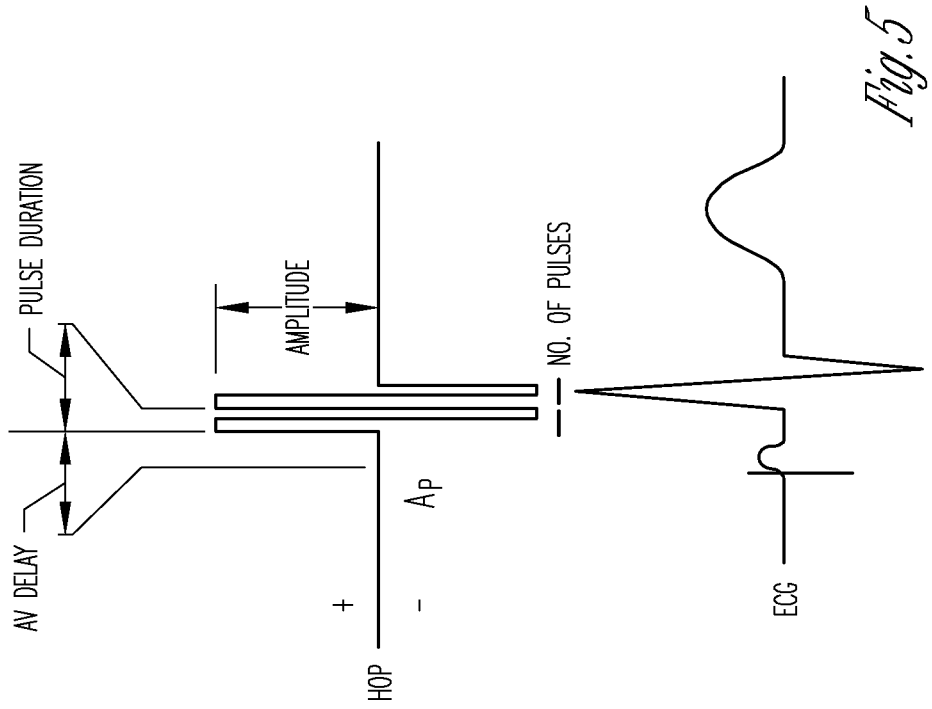
FIG. 4 illustrates a HOP mode.
Figure 5:
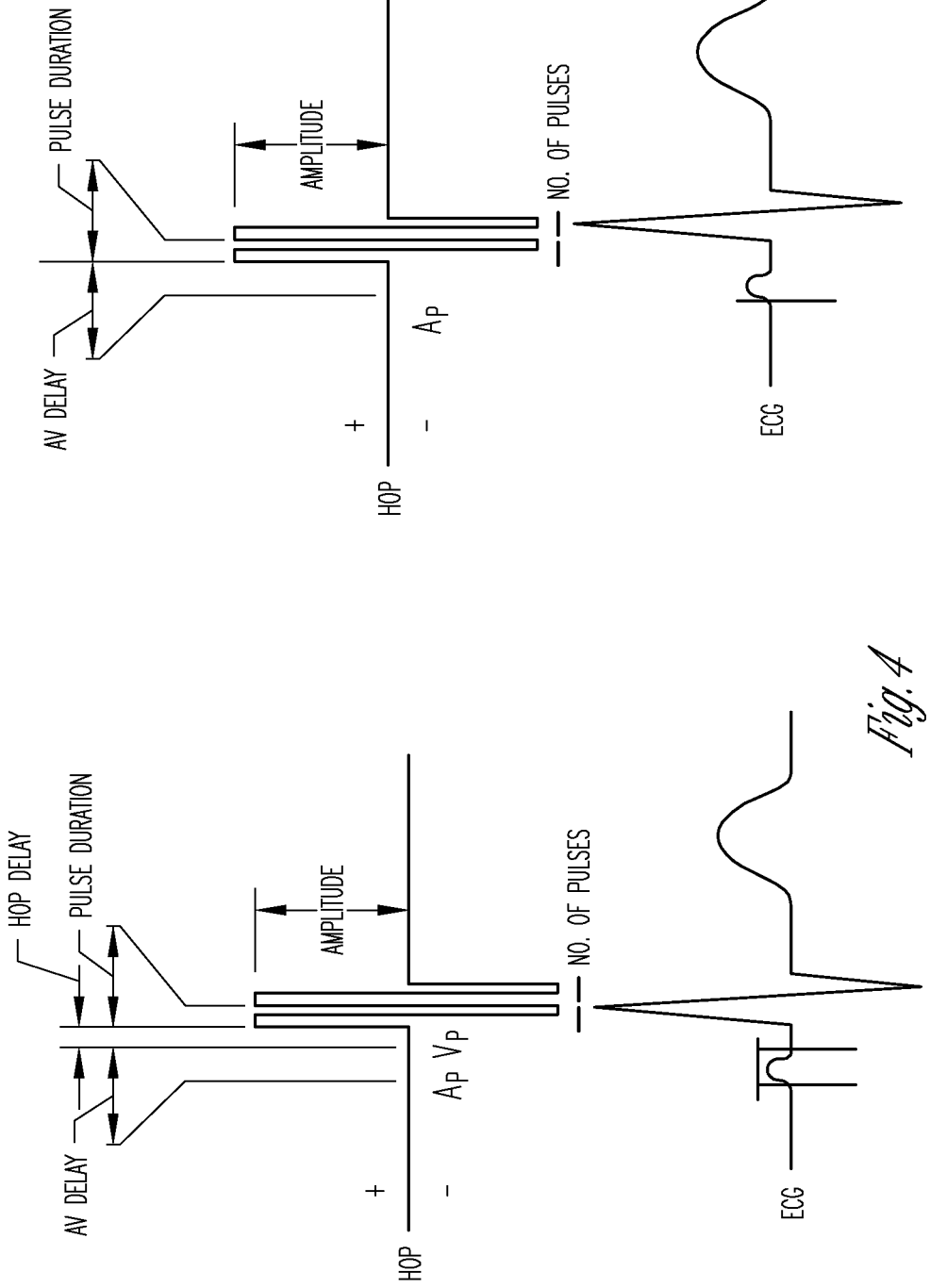
FIG. 5 illustrates a HOP mode.

As described above, HOP therapy for augmenting myocardial contractility requires optimization of stimulation parameters for consistent results. The controller of the implantable pacing device may be programmed to perform an optimization procedure to select optimal stimulation parameters for delivering HOP. In such a procedure, the controller cycles through selected sets of different stimulation parameters while delivering HOP and measures the hemodynamic response to each stimulation parameter set using one or more of the device's sensing modalities. One stimulation parameter that may be included in the parameter set is the stimulation site (or sites) to which HOP stimulation is delivered. The device may be implanted with multiple leads and/or multipolar leads that allow disposition of stimulation electrodes at a plurality of different endocardial or epicardial sites. One site that has been found to often be responsive is the anterior and posterior AV groove at the level of the valve. The controller utilizes the switch matrix to select different stimulation electrodes for delivering HOP to different sites during the optimization procedure. Other stimulation parameters that can be included in a parameter set relate to the stimulation pulse waveform and the timing for delivering the pulses. As noted above, HOP can be delivered as high-energy excitatory pulses in accordance with a bradycardia pacing mode, referred to herein as Mode 2. The HOP stimulation pulse is of longer duration than a conventional pacing pulse, and the duration of the pulse PD is a parameter that affects the contractility response. HOP can also be delivered during the refractory period following a ventricular pace, referred to herein as Mode 1. The stimulation pulse waveform for Mode 1 may be similar to that used for Mode 2, and the pulse duration PD may be similarly adjusted for maximal contractility response. Another stimulation parameter for Mode 1 is the delay DLY between the ventricular pacing pulse and the HOP stimulation pulse delivered during the refractory period. FIGS. 4 and 5 illustrate the timing of the stimulation pulses for Modes 1 and 2, respectively, as delivered in an atrial tracking mode in relation to an ECG. FIG. 4 shows a HOP stimulation pulse of duration PD that follows a ventricular pacing pulse $V_p$ by a delay DLY. FIG. 5 shows an excitatory HOP stimulation pulse of duration PD. For both modes, the AV delay following an atrial pace $A_p$ (or an atrial sense) for delivering the ventricular pacing pulse or the excitatory HOP pulse is another stimulation parameter that may be optimized. Another parameter that may be optimally adjusted for both modes is the type (e.g., number of phases, amplitude) of the HOP stimulation waveform.

Figure 6:
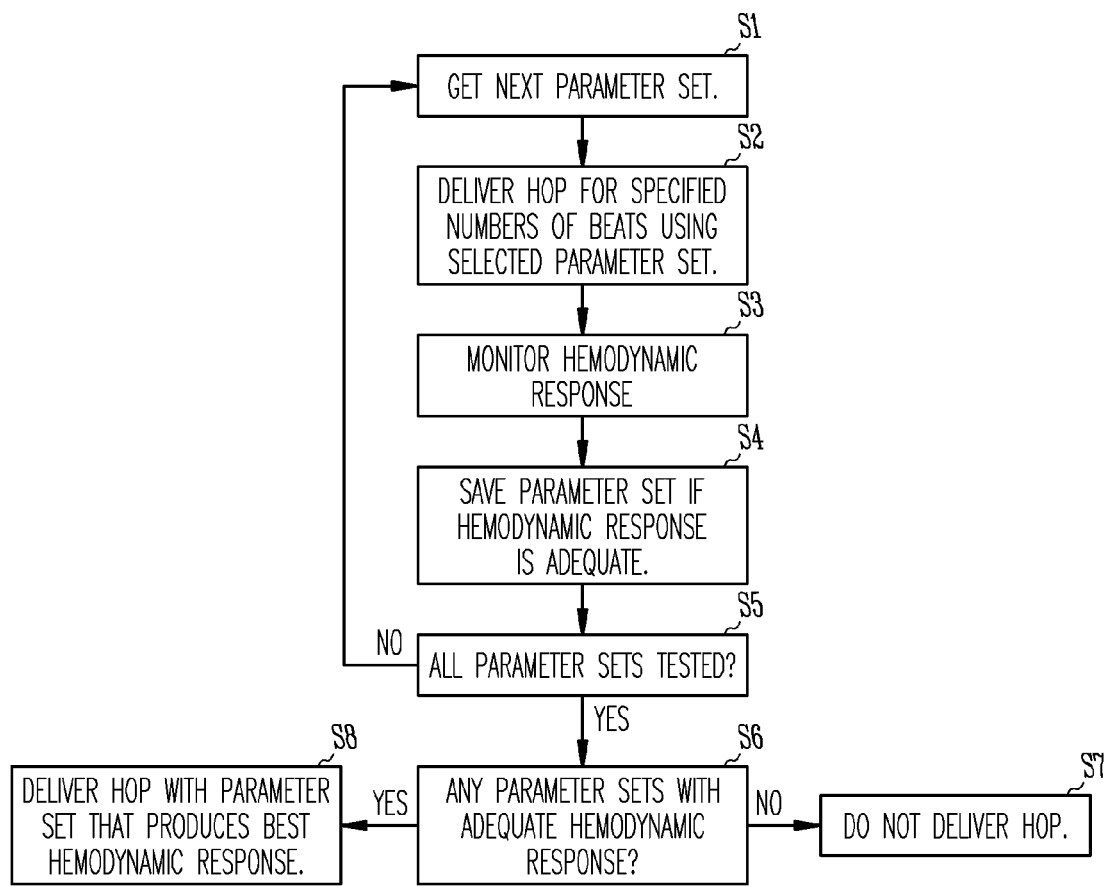
FIG. 6 illustrates an exemplary procedure for optimizing HOP stimulation.

FIG. 6 illustrates an exemplary optimization procedure that may be executed by the device controller. Such an optimization procedure may be executed at periodic intervals, upon command, in response to sensed parameters or events, or whenever the HOP mode is entered if the HOP is delivered intermittently. At step S1, a particular parameter set is selected from a list of parameter sets to be tested, where the parameter set may specify the HOP mode (e.g., Mode 1 or Mode 2), the stimulation site or sites, the stimulation pulse duration PD, the delay DLY if Mode 1 is selected, and/or the AV delay for delivering a ventricular pace or HOP stimulation pulse in an atrial tracking pacing mode. At step S2, HOP is delivered for a specified number of beats using the selected parameter set while the hemodynamic response is concurrently monitored at step S3. As discussed earlier, in order to measure the hemodynamic response, the device is equipped with the capability of measuring one or more physiological variables that are reflective of myocardial contractility. Examples of such variables include heart sound amplitudes (e.g., the amplitude of the sound mitral valve closure during systole), systolic blood pressure, or cardiac stroke volume (e.g., as measured by a transthoracic impedance sensor). At step S4, hemodynamic response is evaluated (e.g., by comparing the physiological variables to specified threshold values over the specified number of beats), and the selected parameter set and hemodynamic response is saved if the hemodynamic response is deemed adequate. Adequacy of the hemodynamic response may depend upon both the magnitude and the consistency of the hemodynamic response over the specified number of beats. At step S5, the procedure loops back to step S1 if there are still parameter sets in the list to be tested. Otherwise, at step S6, it is determined whether any of the parameter sets in the list have produced an adequate hemodynamic response. If not, the controller discontinues (or does not initiate) HOP at step S7. Otherwise, the controller delivers HOP using the saved parameter set that produces the best hemodynamic response at step S8.

3. Delivery of Intermittent High-Output Pacing Stimulation

As described above, HOP stimulation of the heart can be used to improve systolic function in HF patients by increasing myocardial contractility. Chronic HOP stimulation of the heart, however, could overstress the heart in certain HF patients and be hazardous. Accordingly, in such patient, HOP stimulation should be delivered on an intermittent basis. The pacing device controller may be configured to deliver intermittent HOP stimulation by switching from a normal operating mode to a HOP stimulation mode. In the normal operating mode, the device may deliver no therapy at all or may be configured to delivery therapies such as bradycardia pacing, cardiac resynchronization pacing, and/or shocks or anti-tachycardia pacing in response to detection of tachyarrhythmias.

Figure 7:
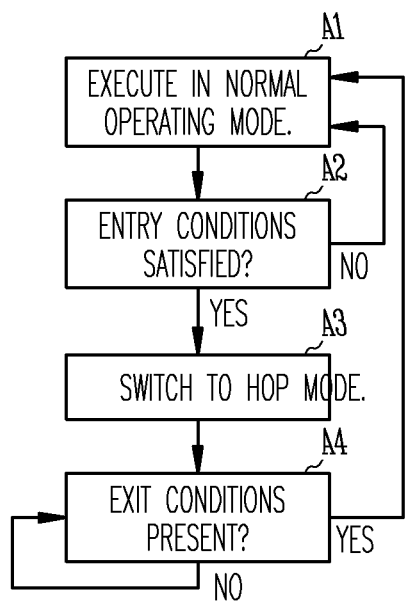
FIG. 7 illustrates an exemplary algorithm for controlling entry and exit into the HOP mode.

The device may be configured to use one or more entry and/or exit conditions in controlling entry and/or exit into the HOP mode. An entry or exit condition could be, for example, a lapsed time interval (e.g., specified time(s) of the day), actuation of a switch by the patient (e.g., a magnetically or tactilely actuated switch interfaced to the device controller), a command received via telemetry, detection or non-detection of a condition such as upright posture, or a measured variable being within or out of a specified range. Examples of such measured variables include heart rate, activity level, minute ventilation, cardiac output, heart sounds, and blood pressure. Entry and/or exit conditions may also be composite conditions where a plurality of entry and/or exit conditions are logically ORed or ANDed together to determine whether a composite entry or entry condition is satisfied. FIG. 7 illustrates an exemplary algorithm executable by the device controller for controlling entry and exit into the HOP mode. As shown in the figure, the controller of the device is programmed to transition through a number of different states, designated as A1 through A4. At state A1, the device operates in its normal operating mode. At state A2, while continuing to operate in state A1, the device determines whether it should switch to the HOP mode by testing for one or more particular entry conditions. If an entry condition is satisfied, the device switches to the HOP mode at step A3. Examples of entry conditions that must be satisfied before the switch to the HOP mode include a measured exertion level being within a specified entry range (where exertion level may be measured by, e.g., heart rate, activity level, or minute ventilation), non-detection of cardiac arrhythmias, non-detection of cardiac ischemia, receipt of a telemetry command, and actuation by the patient of a magnetically or tactilely actuated switch incorporated into the device that allows switching to the HOP mode. While executing in the HOP mode, the device monitors for one or more exit conditions which cause the device to revert to the normal operating mode. Such exit conditions could be the same or different from the entry conditions that must be satisfied before entering the HOP mode. Examples of exit conditions include a measured exertion level being outside a specified permissible range, a measured heart rate being outside a specified permissible range, presence of a cardiac arrhythmia, presence of cardiac ischemia, receipt of a telemetry command, and actuation by the patient of a magnetically or tactilely actuated switch incorporated into the device by the patient to stop delivery of HOP stimulation. If an exit condition occurs, the device returns to the normal operating mode at state A1.

4. Delivery of High-Output Pacing Stimulation in Response to Detection of Decompensation Cardiac failure refers to a condition in which the heart fails to pump enough blood to satisfy the needs of the body, usually due to some damage to the heart itself, such as from a myocardial infarction or heart attack. When heart failure occurs acutely, autonomic circulatory reflexes are activated that both increase the contractility of the heart and constrict the vasculature as the body tries to defend against the drop in blood pressure. Venous constriction, along with the reduction in the heart's ability to pump blood out of the venous and pulmonary systems (so-called backward failure), causes an increase in the diastolic filling pressure of the ventricles. This increase in preload (i.e., the degree to which the ventricles are stretched by the volume of blood in the ventricles at the end of diastole) causes an increase in stroke volume during systole, a phenomena known as the Frank-Starling principle. If the heart failure is not too severe, this compensation is enough to sustain the patient at a reduced activity level. When moderate heart failure persists, other compensatory mechanisms come into play that characterize the chronic stage of heart failure. The most important of these is the depressing effect of a low cardiac output on renal function. The increased fluid retention by the kidneys then results in an increased blood volume and further increased venous return to the heart. A state of compensated heart failure results when the factors that cause increased diastolic filling pressure are able to maintain cardiac output at a normal level even while the pumping ability of the heart is compromised.

Compensated heart failure, however, is a precarious state. If cardiac function worsens or increased cardiac output is required due to increased activity or illness, the compensation may not be able to maintain cardiac output at a level sufficient to maintain normal renal function. Fluid then continues to be retained, causing the progressive peripheral and pulmonary edema that characterizes overt congestive heart failure. Diastolic filling pressure becomes further elevated which causes the heart to become so dilated and edematous that its pumping function deteriorates even more. This condition, in which the heart failure continues to worsen, is decompensated heart failure. It can be detected clinically, principally from the resulting pulmonary congestion and dyspnea, and all clinicians know that it can lead to rapid death unless appropriate therapy is instituted.

Decompensated heart failure is primarily a result of the heart failing to pump sufficient blood for the kidneys to function adequately and maintain fluid balance. When cardiac output falls, renal perfusion decreases which results in reduced glomerular filtration and reduced urine output. The decreased blood flow to the kidneys also activates the rennin-angiotensin system which further reduces renal perfusion and promotes the reabsorption of water and salt from the renal tubules. In the latter stages of this process, angiotensin stimulates secretion of aldosterone which causes a further increase in the reabsorption of sodium. The increase in sodium reabsorption raises the osmolarity of the blood which then elicits secretion of vasopressin and increased tubular reabsorption of water. Excess fluid retention brought about by renal compensation for heart failure has a diluting effect on the blood, thus decreasing the patient's hematocrit, where the hematocrit is defined as the percentage of red blood cells in the blood.

By monitoring the fluid status of a patient (e.g., hematocrit and/or plasma osmolarity), the physiologic changes leading to decompensated heart failure may be detected at an early stage before clinical symptoms become apparent. An implantable device for monitoring a patient's fluid status in order to detect cardiac decompensation is described in U.S. Pat. No. 7,356,366, assigned to Cardiac Pacemakers, Inc. and hereby incorporated by reference. Accordingly, the implantable device for delivering HOP therapy as described herein may be similarly equipped with sensor(s) for measuring the patient's hematocrit, plasma osmolarity, or other parameters indicative of fluid status. The device then compares the fluid status parameter to a threshold value and, if a deviation from the threshold value to a predetermined extent is found, decompensation is detected. The device then uses such detection of decompensation as an entry condition for initiating HOP therapy in order to improve systolic function. The device may also be configured to detect other variables that are correlated with cardiac decompensation to trigger HOP therapy such as an augmented S3 heart sound as detected with an accelerometer, changes in heart rate including increasing sympathetic tone as detected from heart rate variability, changes in the patient's weight as communicated to the device via telemetry, detection of pulmonary edema or changes in breathing patterns via an impedance sensor, an increase in pulmonary artery pressure (or other blood pressure changes) as detected by an indwelling pressure sensor connected to the device, or changes in cardiac stroke volume as detected by an impedance sensor. Any these variables may be used alone or in combination as entry conditions for triggering HOP therapy in order to treat decompensation. Alternatively, direct sympathetic neural stimulation (stellate ganglion, etc) may be performed upon detection of the decompensation event or such sympathetic nerve stimulation may be combined with HOP for enhanced effect. Methods and devices for such neural stimulation are described in co-pending U.S. patent application Ser. No. 11/539,301, now issued as U.S. Pat. No. 7,664,548, assigned to Cardiac Pacemakers, Inc. and hereby incorporated by reference. Once initiated, HOP therapy for treating decompensation may be terminated after a programmed exit condition (e.g., lapsing of predetermined time interval, detection of an arrhythmia, or receipt of command) occurs as described above.

5. Delivery of Intermittent High-Output Pacing Stimulation Based Upon Circadian Patterns As described above, HOP therapy may be initiated upon detection of an entry condition that indicates a decrease in myocardial contractility. Myocardial contractility may be monitored, for example, by measuring the amplitude of heart sounds via an accelerometer, employing a lead-based contractility measure (e.g., a fiber-optic lead), measuring changes in systolic blood pressure with an indwelling pressure monitor, or detecting changes in cardiac stroke volume or cardiac output via an impedance measurement. The HOP therapy then serves to counteract the detected decrease in myocardial contractility to at least partially restore normal systolic function. Another way that HOP therapy may be employed for beneficial effect, however, is to condition the myocardium even when systolic function is normal. HOP therapy delivered in this manner may mimic the effects of exercise and strengthen the heart muscle. Accordingly the device may be programmed to deliver HOP therapy when it is most convenient for the patient and/or likely to have the most beneficial effect. One way to deliver HOP therapy in this situation is based upon the patient's circadian patterns. The device may be configured to detect such circadian patterns based upon, for example, the actual time of day as detected by the device's internal timer, indications of posture change as detected by a multi-axis accelerometer, changes in heart rate or breathing patterns, and changes in autonomic balance as detected from heart rate variability. The device may then be programmed to estimate when the patient is sleeping and use the estimate as an entry condition for initiating HOP therapy. For example, the device may be programmed to deliver HOP therapy either continuously or for short time periods within a night and terminate the HOP upon detection of an arrhythmia (or pro-arrhythmic condition) or detection of sleep disordered breathing such as apnea.

The invention has been described in conjunction with the foregoing specific embodiments. It should be appreciated that those embodiments may also be combined in any manner considered to be advantageous. Also, many alternatives, variations, and modifications will be apparent to those of ordinary skill in the art. Other such alternatives, variations, and modifications are intended to fall within the scope of the following appended claims.

What is claimed is:

1. A cardiac rhythm management device, comprising:
pulse generation circuitry for delivering electrical stimulation to one or more electrodes;
a switching matrix for connecting the pulse generation circuitry to one or more of a plurality of available electrodes disposed at a plurality of stimulation sites;
a hemodynamic response sensor for sensing a physiological variable reflective of myocardial contractility;
a controller programmed to, in a normal mode, deliver pacing pulses to a selected stimulation site using a bradycardia pacing mode;
wherein the controller is programmed to, in a high-output pacing (HOP) mode, deliver pacing pulses to an optimal HOP stimulation site using a bradycardia pacing mode with a pacing pulse energy greater than in the normal mode;
wherein the controller is programmed to cycle through a plurality of different stimulation sites by operating the switch matrix to connect the pulse generator to different ones of the available electrodes in order to deliver HOP stimulation to the different stimulation sites, compare the hemodynamic response sensor outputs of each of the different stimulation sites white HOP stimulation is delivered thereto, and select the optimal HOP stimulation site based upon the comparison;
sensing circuitry for detecting cardiac decompensation;
wherein the controller is programmed to operate in the normal mode and to intermittently enter and exit the HOP mode in accordance with specified entry and exit conditions; and,
wherein the device is programmed to use detection of cardiac decompensation as an entry condition for triggering delivery of HOP stimulation in the HOP mode.

2. The device of claim 1 wherein the sensing circuitry for detecting cardiac decompensation includes a sensor for measuring a patient's plasma osmolarity.

3. The device of claim 1 wherein the sensing circuitry for detecting cardiac decompensation includes a sensor for measuring a patient's hematocrit.

4. The device of claim 1 wherein the sensing circuitry for detecting cardiac decompensation includes an accelerometer for detecting heart sounds.

5. The device of claim 1 wherein the sensing circuitry for detecting cardiac decompensation includes an impedance sensor for detecting pulmonary edema or changes in breathing patterns.

6. The device of claim 1 wherein the sensing circuitry for detecting cardiac decompensation includes one or more sensors for measuring a physiological variable related to myocardial contractility.

7. The device of claim 1 wherein the sensing circuitry for detecting cardiac decompensation includes a sense amplifier for incorporation into a sensing channel for detecting heart rate and for detecting increasing sympathetic tone as derived from heart rate variability.

8. The device of claim 1 wherein the sensing circuitry for detecting cardiac decompensation includes a transceiver for receiving changes in a patient's weight as communicated to the device via telemetry.

9. The device of claim 1 wherein the sensing circuitry for detecting cardiac decompensation includes an indwelling pressure sensor connected to the device for detecting an increase in pulmonary artery pressure or other blood pressure changes.

10. The device of claim 1 wherein the sensing circuitry for detecting cardiac decompensation includes an impedance sensor for detecting changes in cardiac output.

11. The device of claim 1 wherein the hemodynamic response sensor is selected from a heart sound sensor, an accelerometer, a pressure sensor, or a transthoracic impedance sensor.

12. A method, comprising:
configuring a cardiac device to deliver stimulation to one or more myocardial stimulation sites through one or more stimulation channels by connecting pulse generation circuitry to one or more of a plurality of available electrodes;
configuring the device to sense a physiological variable reflective of myocardial contractility and detect cardiac decompensation;
programming a controller of the device to, in a normal mode, deliver pacing pulses to a selected stimulation site using a bradycardia pacing mode and, in a high-output pacing (HOP) mode, deliver pacing pulses to an optimal HOP stimulation site using a bradycardia pacing mode with a pacing pulse energy greater than in the normal mode;
programming the controller to cycle through a plurality of different stimulation sites by operating the switch matrix to connect the pulse generator to different ones of the available electrodes in order to deliver HOP stimulation to the different stimulation sites, to compare the hemodynamic response sensor outputs of each of the different stimulation sites while HOP stimulation is delivered thereto, and to select the optimal HOP stimulation site based upon the comparison;
programming the controller to operate in the normal mode and to intermittently enter and exit the HOP mode in accordance with specified entry and exit conditions; and,
programming the controller to use detection of cardiac decompensation as an entry condition for triggering delivery of HOP stimulation in the HOP mode.

13. The method of claim 12 further comprising configuring the device to detect cardiac decompensation by measuring a patient's plasma osmolarity.

14. The method of claim 12 further comprising configuring the device to detect cardiac decompensation by measuring a patient's hematocrit.

15. The method of claim 12 further comprising configuring the device to detect cardiac decompensation by using an accelerometer for detecting heart sounds.

16. The method of claim 12 further comprising configuring the device to detect cardiac decompensation by using an impedance sensor for detecting pulmonary edema or changes in breathing patterns.

17. The method of claim 12 further comprising configuring the device to detect cardiac decompensation by using an indwelling pressure sensor connected to the device for detecting an increase in pulmonary artery pressure or other blood pressure changes.

18. The method of claim 12 wherein the sensed physiological variable sensor is selected from heart sounds, blood pressure, or cardiac stroke volume.

* * * * *